(12) United States Patent  
Curtis (10) Patent No.: US 7,609,813 B2
(45) Date of Patent: Oct. 27, 2009

(54) SYSTEM AND METHOD FOR IMPROVED COLLISION DETECTION IN AN IMAGING DEVICE

(75) Inventor: Steven E. Curtis, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 469 days.

(21) Appl. No.: 11/557,796

(22) Filed: Nov. 8, 2006

(65) Prior Publication Data

US 2008/0123811 A1    May 29, 2008

(51) Int. Cl.
*H05G 1/08* (2006.01)
*G05B 13/04* (2006.01)

(52) U.S. Cl. .................... 378/91; 378/196; 378/197; 318/560; 318/561

(58) Field of Classification Search .............. 378/91, 378/117, 196, 197, 198; 318/560, 561
See application file for complete search history.

(56) References Cited

U.S. PATENT DOCUMENTS

| | | | |
|---|---|---|---|
| 3,566,112 A | 2/1971 | Luecke | |
| 4,506,321 A | 3/1985 | Comstock et al. | |
| 4,609,855 A * | 9/1986 | Andrews | 318/561 |
| 4,673,261 A | 6/1987 | Hunt et al. | |
| 4,761,595 A | 8/1988 | Goor | |
| 5,485,502 A * | 1/1996 | Hinton et al. | 378/117 |
| 5,710,496 A * | 1/1998 | Boom | 318/610 |
| 5,726,877 A | 3/1998 | Antoszkiewicz et al. | |
| 5,878,112 A * | 3/1999 | Koertge | 378/209 |
| 6,185,340 B1 | 2/2001 | Comer | |
| 6,272,368 B1 * | 8/2001 | Alexandrescu | 600/407 |
| 6,940,685 B2 * | 9/2005 | Chrappan Soldavini et al. | 360/78.06 |
| 7,029,175 B2 * | 4/2006 | Karaus et al. | 378/197 |
| 7,034,492 B2 * | 4/2006 | Curtis | 318/610 |
| 7,130,378 B2 * | 10/2006 | Akutsu et al. | 378/117 |
| 2002/0164560 A1 | 11/2002 | Borta | |
| 2004/0012722 A1 | 1/2004 | Alvarez | |
| 2004/0234039 A1 | 11/2004 | Karaus et al. | |
| 2004/0239702 A1 | 12/2004 | Kang et al. | |
| 2005/0028014 A1 | 2/2005 | Allred et al. | |
| 2005/0088132 A1 | 4/2005 | Curtis | |
| 2006/0087274 A1 | 4/2006 | Curtis | |
| 2006/0087632 A1 | 4/2006 | Tousain | |

\* cited by examiner

*Primary Examiner*—Allen C. Ho
(74) *Attorney, Agent, or Firm*—McAndrews, Held & Malloy, Ltd.; Peter J. Vogel; Michael A. Dellapenna

(57) ABSTRACT

An imaging system that includes a radiation source. An image receptor is located to receive radiation emitted by the radiation source. The imaging system further has a servo system that includes a computer operationally coupled to a motor-load element. The servo system is configured to position the radiation source, the image receptor and the object to be scanned. The servo system is configured to measure at set time intervals in real-time a position of the radiation source, the image receptor, and the object. The measured position is used to predict a native hardware motion parameter value for the servo system.

20 Claims, 6 Drawing Sheets

FIG. 3
Native Motor-Load Model

FIG. 4A

Presumed (errant) hardware parameters and associated compensation, deviating from actual parameters
- Torque Constant (2X error)
- Inductance (0.5X error)
- Inertia (0.5X error)

Motion system input forcing function & output response plotting position against time.

FIG. 4B

Feedback error signal (input minus output delta), plotting position error against time.

Bad Collision to Acceleration signal ratio (negative ringing, etc.)

FIG. 4C

Actual (correct) hardware parameters and associated compensation that could be obtained with the adaptive correction technique:
- Torque Constant (no error)
- Inductance (no error)
- Inertia (no error)

Motion system input forcing function & output response plotting position against time.

— Xin(T)
---- Yout(T)

FIG. 4D

Feedback error signal (input minus output delta), plotting position error against time.

— Xin(T) – Feedback(T-1)
--- x 10k Collision X2(T)

FIG. 5

SYSTEM AND METHOD FOR IMPROVED COLLISION DETECTION IN AN IMAGING DEVICE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to a system and method for improved collision detection between a movable component of an imaging device and an object. In particular, the present invention relates to improved collision detection using a real-time process for adaptively obtaining motion parameters of a movable component of an imaging system.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays, for example. The generated images may be used for many purposes in analyzing the object such as detecting internal defects, determining changes in internal structure or alignment, or tracking fluid flow within the object. Furthermore, the image may show the presence or absence of certain elements in an object. The information gained from medical diagnostic imaging has applications in many fields, including medicine and manufacturing.

Medical diagnostic imaging systems often require the motion of a subsystem in proximity to an object. For example, in acquiring fluorographic images, an x-ray source and image sensor are moved to various locations about a patient to obtain multiple views of the patient's anatomy. In another example such as acquiring CT slice data, an x-ray source and/or sensor are rotated about a patient to obtain the desired imaging. As the subsystem moves about the object to obtain the medical diagnostic data, collisions may occur with the patient or other objects in proximity to the moving subsystem.

Movement of a diagnostic imaging subsystem is typically accomplished using a servo system, that is, an electromechanical system that performs mechanical movement generally using software control along with feedback. A collision or impending collision of a moving subsystem with an object generally is monitored using one of two types of anti-collision sensors: contact sensors and proximity sensors, which typically are associated with bumpers or other targeted regions on the diagnostic imaging system. Monitoring and adjustments for collisions or impending collisions can also be accomplished using feedback and/or feed forward processes within the servo system of the diagnostic imaging system.

It is important in a diagnostic imaging system to obtain early detection of a collision between a moving subsystem and a patient, or other obstruction. The use of feedback signals can provide more universal sensing capability than the use of contact and proximity sensors because feedback signals can provide information on resistance to a directed motion anywhere along the moving subsystem. However, normal operation of a servo system can also create feedback signals that are not due to a collision but are similar to a signal that a collision would induce. Additionally, feedback and/or feed forward signals may be processed in a way that allows a diagnostic imaging system to inherently be less aggressive in powering motion against a collision, while at the same time retaining the desired aggressiveness in powering motion resulting from an input control signal.

Motion control signals associated with feedback for a moving subsystem of a diagnostic imaging device can be monitored to sense a collision. Monitoring data from motion control signals associated with feedback can be used to prevent false collision detection that can occur due to feedback signals. Furthermore, the use of feed forward can suppress a collision, thereby lowering the chance that the collision creates motion problems or damage associated with the moving subsystem of the imaging devices. Feed forward is useful for optimizing the collision detection performance of a moving subsystem in an imaging device. However, the accuracy of feed forward decreases when presumed motion parameters that are associated with the hardware of a servo system for a moving subsystem do not reflect the actual servo system hardware. In general, inaccuracies in the motion parameters associated with all aspects of the moving subsystem hardware can detract from collision detection. Furthermore, feed forward can be particularly sensitive to degradation due to errors in the presumed values of hardware motion parameters.

Thus, there is a need for systems and methods for obtaining and using enhanced hardware motion parameters for moving subsystems to improve collision detection in imaging systems.

BRIEF DESCRIPTION OF THE INVENTION

Certain embodiments of the present disclosure provide an imaging system that includes a radiation source, an image receptor located to receive radiation emitted by the radiation source, and a servo system. The servo system includes a computer operationally coupled to a motor-load element. The servo system is configured to position at least one of the radiation source, the image receptor, and an object to be scanned. The servo system is further configured to measure at set time intervals in real-time a position of at least one of the radiation source, the image receptor, and the object. The measured position is used to predict a native hardware motion parameter for the servo system.

Certain embodiments of the present disclosure provide a method of improving collision detection between an object and an electromechanical system having a mechanical output controlled by a servo system. The method includes determining servo system motor-load element parameter values in real-time, predicting in a native motor-load model a motion control parameter value for a motor-load element of the servo system using at least one of the real-time servo system motor-load element parameter values, and applying the predicted motion control parameter value to an operation within a computer element of the servo system to enhance a control signal output from the computer element to the motor-load element of the servo system.

Certain embodiments of the present disclosure provide a computer-readable medium having a set of instructions for execution on a computer. The set of instructions includes a monitoring routine for determining a servo system motor-load element parameter value in real-time, a prediction routine for applying the real-time servo system motor-load parameter value into a native motor-load model to predict a motion control parameter value, and a control signal routine that applies the predicted motion control parameter value to an operation that modifies a control signal output of a computer element of a servo system.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
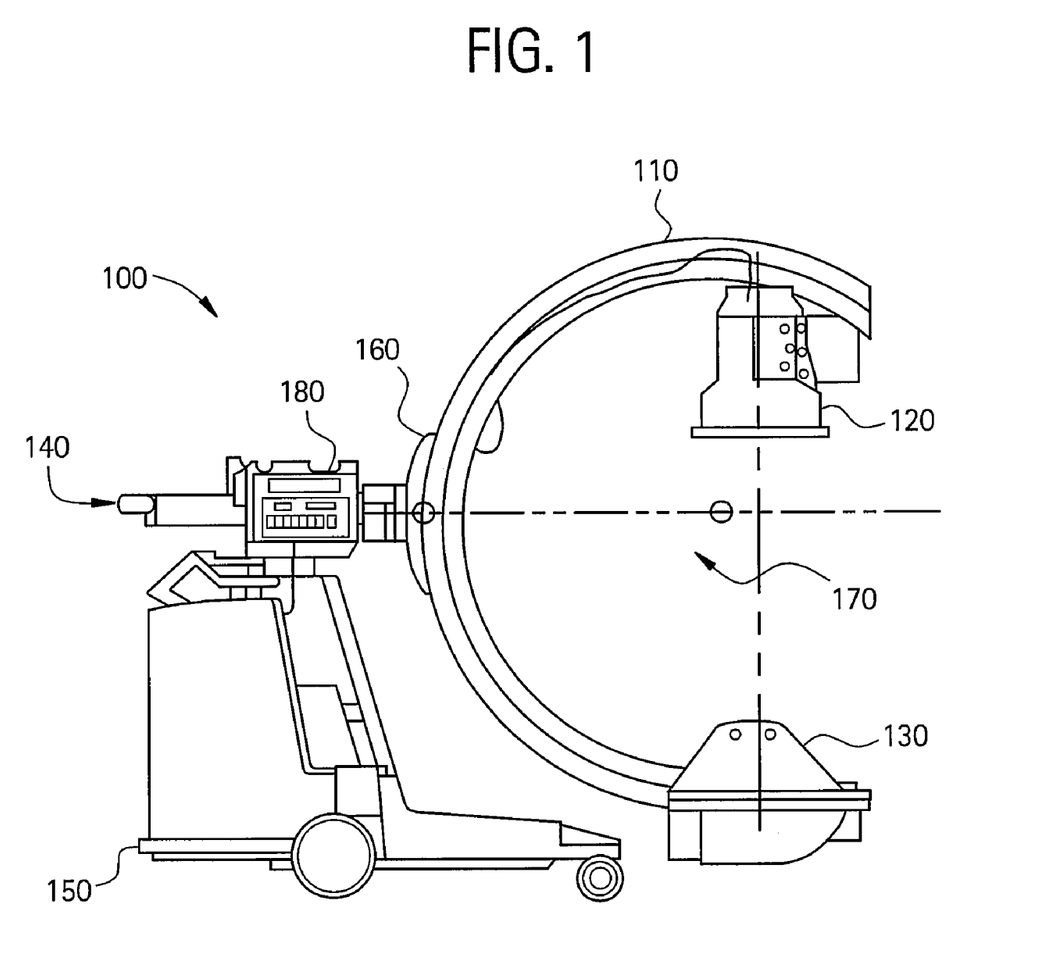
FIG. 1 illustrates a mobile C-arm imaging system according to an embodiments of the present invention.

FIG. 1 illustrates an exemplary embodiment of a mobile C-arm imaging system 100 in which the systems and methods described herein can be implemented. The system 100 includes a C-arm 110, an image receptor 120, a radiation source 130, a support structure 140 and a wheeled base 150. The image receptor 120 and the radiation source 130 can be mounted at opposing locations on the C-arm 110. The support structure 140 can provide support for the C-arm 110 and hold the C-arm 110 in a suspended position. The support structure 140 can be mounted on a wheeled base 150 that allows the system 100 to be moved. Examples of imaging system 100 can include systems based on x-ray imaging, ultrasound imaging, magnetic resonance imaging (MRI), single photon emission computed tomography (SPECT) imaging, computed tomography (CT) imaging and positron emission tomography (PET) imaging.

The support structure 140 provides stable, balanced support for the C-arm 110. The support structure 140 suspends the C-arm 110 for use in imaging a patient or an object, for example. The support structure 140 also allows the C-arm 110 to be rotated about an axis of rotation (manually or using a motor, for example). The support structure 140 can be attached to a wheeled base 150, for example, to reposition the system 100. The wheeled base 150 allows mobility of the system 100 to increase access to imaging for patients, for example.

The C-arm 110 allows the image receptor 120 and the radiation source 130 to be mounted and positioned about an object to be imaged, such as a patient. The C-arm 110 can be a circular C-shaped or an arc-shaped member, for example. The C-arm 110 can further allow selective positioning of the image receptor 120 and the radiation source 130 with respect to the width and length of the patient or other object located within the interior free space of the C-arm 110. Image receptor 120 can be an image intensifier or other energy receptor used in diagnostic imaging, for example. The image receptor 120 and the radiation source 130 can be used to generate a diagnostic image representative of the object being imaged.

A support arm 160 can be slidably mounted to the C-arm 110 and support structure 140 to include the structure and mechanisms necessary to enable selective, sliding orbital motion of C-arm 110 about an axis of orbital rotation to a selected position. The axis of orbital rotation coincides with a center of curvature of C-arm 110 and with an axis of lateral rotation. The support structure 140 can further include mechanisms for laterally rotating support arm 160 selectable amounts about the axis of lateral rotation to a selected lateral position. The combination of sliding orbital motion and lateral rotation allows adjustment of C-arm 110 in multiple degrees of freedom of movement.

In operation, a patient, for example, is placed on a table that is positioned between the image receptor 120 and the radiation source 130 mounted on the C-arm 110. The support structure 140 moves the C-arm 110. Moving the C-arm 100 positions the image receptor 120 and the radiation source 130 at desired locations with respect to the patient. The image receptor 120 can be positioned near the patient in order to improve resulting image quality. Alternatively, the system 100 can be configured to perform automatic motions while simultaneously acquiring images, with the patient located more centrally at the isocentric position in the interior free space 170 of the C-Arm 110 and between the image receptor 120 and the radiation source 130. The image receptor 120 and radiation source 130 can then be moved to rotate about the patient's anatomy. Such automatic motions coupled with simultaneous image acquisition can provide data that is useful for generating computed tomography (CT) images, when the data is manipulated by a computer 180.

With the orbital and lateral rotational capabilities of a C-arm 110, the image receptor 120 and radiation source 130 can be selectively positioned with respect to the length and width of a patient located with an interior free space 170 of C-arm 110. The system 100 can include a servo system, that is, an electromechanical system that performs mechanical movement generally using software control along with feedback, coupled to a computer 180. The sliding orbital movement of C-arm 110 can cause image receptor 120 and radiation source 130 to move along respective arcuate movement paths. In certain embodiments of the present disclosure, image receptor 120 is secured to inner circumference of C-arm 110. Radiation source 130 can also be secured to the inner circumference of C-arm 110.

Certain embodiments described herein can include a contact sensor for use, for example, with an imaging system 100. Image receptor 120 can be moved close to the patient or other object to improve image quality, which also can increase the risk of collision between the image receptor 120 or other part of the C-arm 110 and the patient, table, or other object. Certain embodiments detect a collision between the system 100 and the patient or other object being examined. Collision detection is performed to decrease errors in the system 100 due to impact and overcompensation of the system 100, or to decrease the chance of injury to the patient or object.

In certain embodiments, computer 180 can include a device (not shown), for example, a CD-ROM drive or a card reader, for reading instructions and/or data from a computer-readable medium, such as a rotating disc or solid-state computer storage media, for example. In other embodiments, computer 180 can execute instructions stored in firmware (not shown). Computer 180 can be programmed to perform certain functions described herein. The term computer, as used herein, includes not only integrated circuits that are typically referred to as computers in the field of disclosure, but also processors, microcontrollers, microcomputers, programmable logic controllers, application specific integrated circuits, other programmable circuits, or systems containing combinations thereof.

Although the embodiments described for FIG. 1 refer to a mobile C-arm imaging system, the embodiments described herein apply, as well, to all other imaging modalities, including applications utilizing servo systems in proximity to objects for which it is desirable to enhance collision detection. Furthermore, it is contemplated that the benefits of the present disclosure accrue to non-medical imaging systems such as those systems typically employed in a commercial or a transportation setting, such as, for example, baggage scanning systems for airports, transportation centers, government buildings, office buildings and the like. The benefits of the present disclosure can also apply to micro x-ray, PET and CT systems sized, for example, to study animals.

The systems and methods described herein can be applied in feedback and/or feed forward processes to enhance the detection of an unwanted collision between an electromechanical motion system and some obstacle in the path of the intended motion. The present disclosure can be used to enhance the feed forward or feedback processes in a motion system by adaptively determining, in real time, native hardware motion parameters of an electromechanical motion system, such as those found in an imaging device. Motion parameters determined using real-time information, as opposed to presuming values of motion parameters associated with the electromechanical motion system, can facilitate improved collision detection of the motion system with an object. Specifically, values determined in real time can be incorporated into feedback and/or feed forward in the servo system of the electromechanical motion system, which in turn, can improve the collision detection capabilities in an imaging device.

Figure 2:
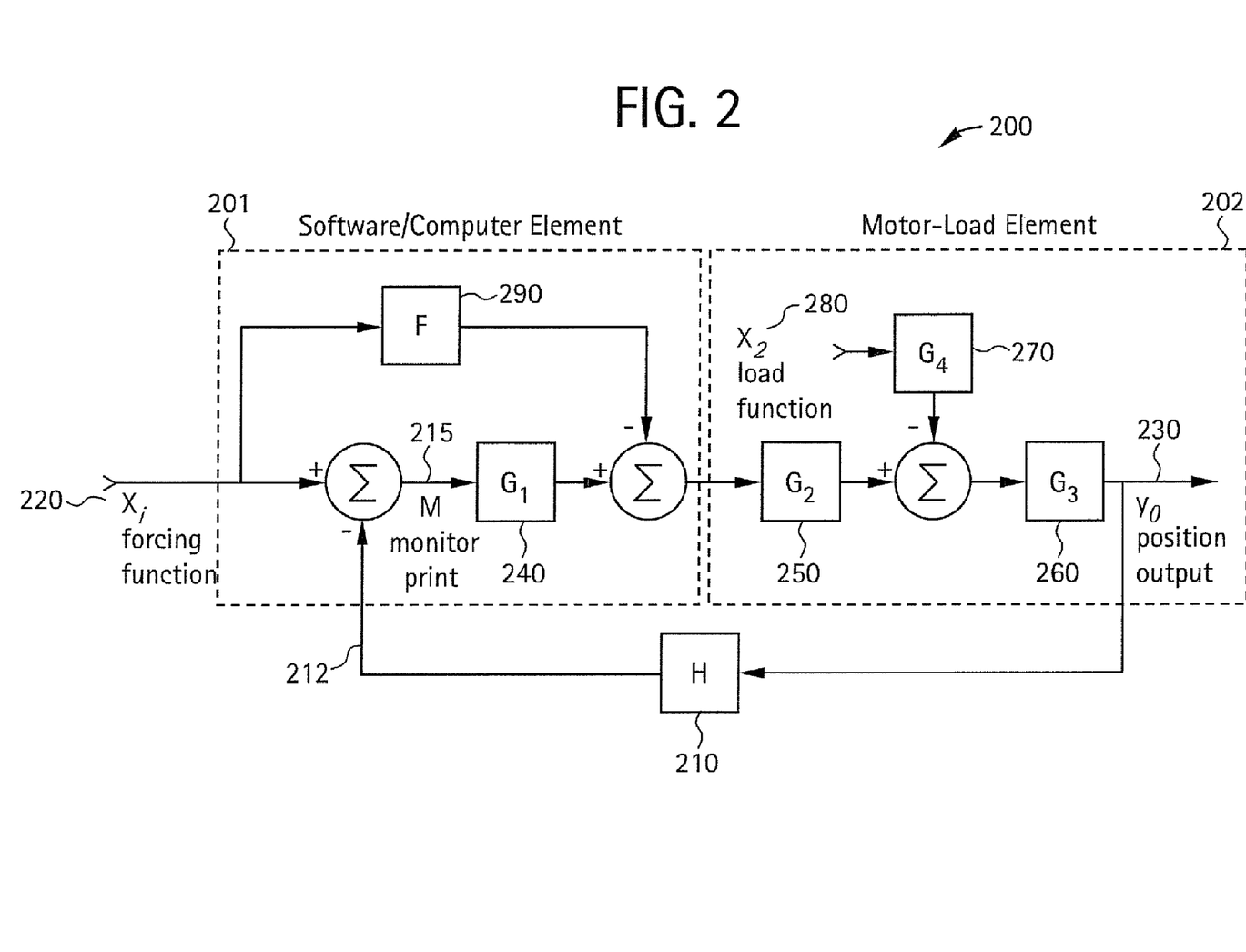
FIG. 2 illustrates a servo system with a feedback controlled motion system according to an embodiment of the present invention.

FIG. 2 schematically illustrates a servo system 200 that can be characterized as having a software/computer element 201 and a motor-load element 202. Servo system 200 can include a feedback mechanism 210 (block H). Feedback mechanism 210 can receive information about motion or position, and convert the information into a signal that can be subtracted from an input forcing function $x_i$ 220. Forcing function $x_i$ 220 is a control signal or digital command that directs the entire servo system 200 to respond, such that a position output or mechanical output $y_o$ 230 moves in an intended way. Block $G_1$ 240 represents the software or mechanism for processing data in a computer, for example, in the servo system structure. Blocks $G_2$, $G_3$ and $G_4$ 250, 260, 270 represent various parts of the servo system motor-load element 202 such as an electric motor, mechanisms that convert rotation of the motor shaft into a useful motion or position of the device, and the influence of resistance, drag or friction from the load $x_2$ 280, which can be input into the system 200. A monitor point 215, M, provides data to the system which represents the difference between forcing function $x_i$ 220 and feedback 212 from feedback mechanism 210. The value of M is generally small depending on the many parameters that define servo system 200. However, M may temporarily have larger values when servo system 200 is being subjected to certain types of stimulus transients that can be applied through either forcing function $x_i$ 220 or load function $x_2$ 280. In interpreting M, it can be desirable to determine if servo system 200 has encountered an undesired collision-in-progress. Under the condition of a collision-in-progress, servo system 200 performance can be altered to avoid an unwanted result of a collision from a fully executed movement. Feed forward through block F 290 can allow changes to be made in G1 240 that can result in altered, and desirably improved, processing of load function $x_2$ 280 to achieve an enhanced detectability of collisions at M 215 without altering end result processing on forcing function $x_i$ 220, which is presumed to already be optimal. In certain embodiments, block F 290 could be summed into the system 200 at points other than the point shown in FIG. 2, with variations in the results. Also, monitor point M 215 can be placed at locations other than that shown in FIG. 2, with variations in the results. Furthermore, multiple points for injecting feedback 212 can be used, in addition to the point shown in FIG. 2. Depending on the characteristics of a servo system, the placement of feed forward injection, monitoring point M and feedback will vary.

In determining motion parameters for servo system 200 based on real-time information, it is desirable to use certain data. In the embodiment of a DC motor, for example, such data can include information that is known ahead of time, such as motor resistance R or rotation-to-position gain constant $K_3$. Such data can also include information provided on an on-going basis from data already available within the computer element 201, such as data representing the motor voltage $V_m(t)$. Such data can further include information sampled in the operation of feedback mechanism 210 of servo system 200, such as position $y_o(t)$ 230. The provision or sampling of data generally occurs at a sample period that can be defined as T. Thus, certain real-time data can be provided or sampled and motion control signals can be calculated every T seconds using the real-time data.

Figure 3:
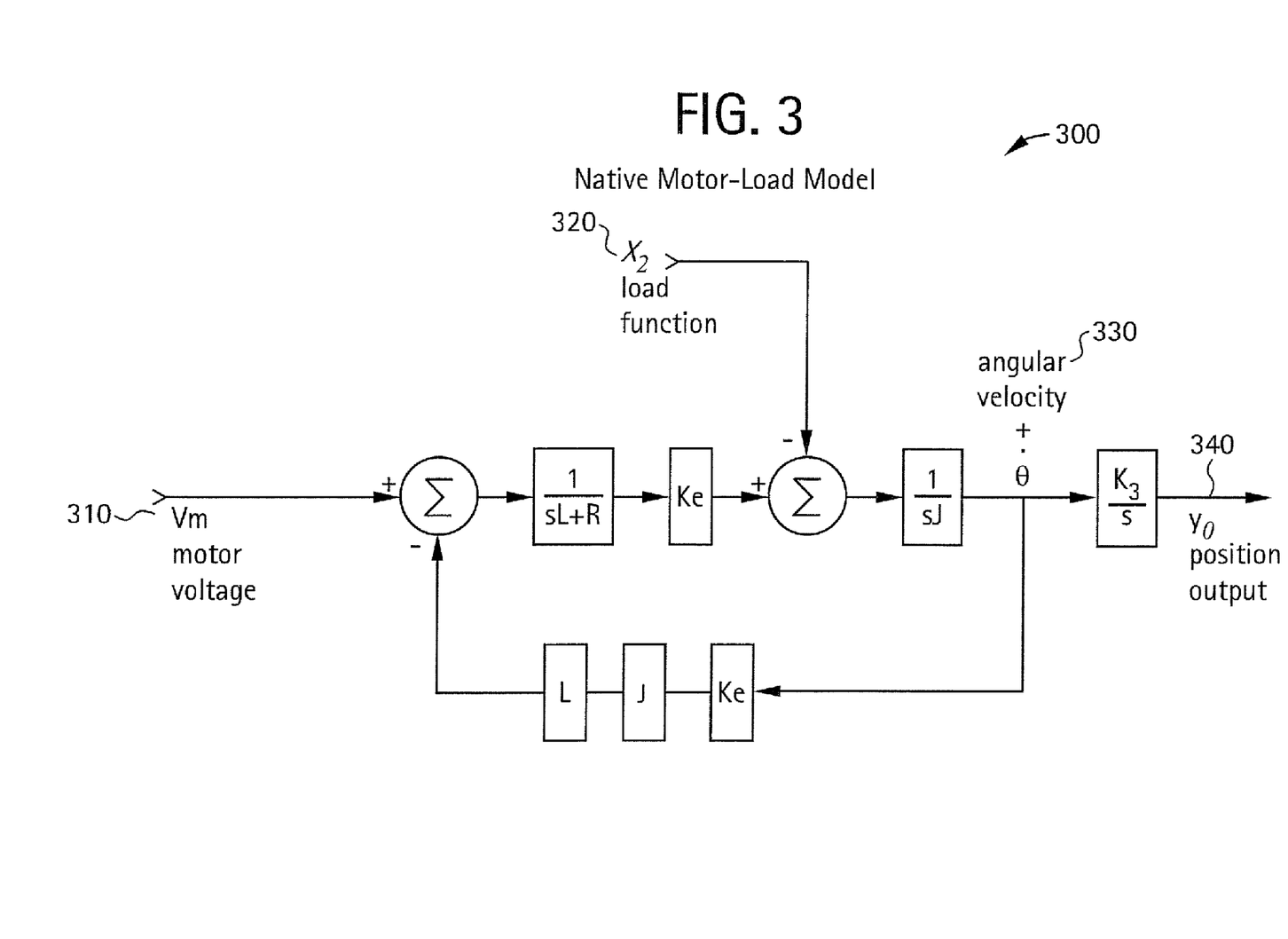
FIG. 3 illustrates a native motor-load model for a servo system according to an embodiment of the present invention.

The various parts of servo system 200 illustrated in FIG. 2 can be represented in the Laplace domain. FIG. 3 illustrates a native motor-load model 300 of the motor-load element of servo system 200. Motor-load model 300 can include several parameters including motor voltage $V_m$ 310, load function $x_2$ 320, motor shaft angular velocity $\dot{s}$ 330, mechanism position output $y_o$ 340, motor inductance L, motor resistance R, motor torque constant $K_e$, mechanical moment of inertia J, rotation-to-position gain constant $K_3$ and Laplace operator s. Mechanical moment of inertia, J, and motor inductance, L, are directly associated with the motion system hardware and can be useful for enhancing feedback and feed forward signals in a servo system.

Inputs for motor voltage $V_m$ 310 and load function $x_2$ 320 into motor-load model 300 can be treated separately by superposition, and by using Mason's law, the following relationships can be developed:

$$\frac{y_0}{V_m} = \frac{\frac{K_e}{sJ(sL+R)}\frac{K_3}{s}}{1+\frac{K_e^2}{sJ(sL+R)}} \qquad (1)$$

-continued $$\frac{y_0}{x_2} = -\frac{\frac{1}{sJ}\frac{K_3}{s}}{1+\frac{K_e^2}{sJ(sL+R)}} \quad (2)$$

Combining equation (1) and equation (2) and further ignoring out-of-band R/L zero associated with the load, modeled position output $y_o$ 340 can be expressed as:

$$y_0 = V_m \frac{\frac{1}{K_e}}{\frac{JL}{K_e^2}s^2+\frac{JR}{K_e^2}s+1}\frac{K_3}{s} - x_2\frac{\frac{R}{K_e^2}}{\frac{JL}{K_e^2}s^2+\frac{JR}{K_e^2}s+1}\frac{K_3}{s} \quad (3)$$

Where:

$$G_2 = \frac{1}{K_e^2}$$

$$G_3 = \frac{K_3}{s}$$

$$G_4 = \frac{R}{K_e^2}$$

Equation (3) can be rearranged for motor-load model 300 and further use of simplifying notation, a and b, gives the following relationship:

$$y_0 = V_m \frac{\frac{K_3}{K_e}}{as^3+bs^2+s} - x_2\frac{\frac{K_3 R}{K_e^2}}{as^3+bs^2+s} \quad (4)$$

where:

$$a = \frac{JL}{K_e^2}$$

$$b = \frac{JR}{K_e^2}$$

Rearrangement of equation (4) gives the following relationship:

$$y_o K_e^2 as^3 + y_o K_e^2 bs^2 + y_o K_e^2 s = V_m K_3 K_e - RK_3 x_2 \quad (5)$$

As discussed in the example of the embodiment shown in FIG. 2, data can be sampled every T seconds, and thus, provide sufficient input data where motion control signals can also be calculated every T seconds in a servo system. Equation (5) can, therefore, be expressed in the sampled time domain by using the approximate z transform identity:

$$s = \frac{2}{T}\frac{z-1}{z+1} \quad (6)$$

Using an operator $z^{-k}$ imposes a delayed signal of k sample periods for the sample period T.

Since the load function $x_2$ is generally constant over the time of interest, a simplifying relationship involving $x_2$ can be established. Substituting equation (6) into equation (5) and applying algebraic manipulation results in $x_2$ being operated on ("multiplied") by $1z^{-0}+3z^{-1}+3z^{-2}+z^{-3}$. However, because $x_2$ has the same value for each of the times mandated by $z^{-0}$, $z^{-1}$, $z^{-2}$, $z^{-3}$, the coefficients 1, 3, 3, 1 can simply be added together to yield the identity:

$$[1+3z^1+3z^2+z^3]x_2R=8x_2R \quad (7)$$

More generally, equation (5) when expressed in the sampled time domain using the transform expressed in equation (6) and when applying the identity of equation (7) yields the following relationship:

$$[1]\frac{8Rx_2}{K_e} + [y_0(t)+y_0(t-1)-y_0(t-2)-y_0(t-3)]\frac{2K_e}{TK_3} + \quad (8)$$
$$[y_0(t)-y_0(t-1)-y_0(t-2)+y_0(t-3)]\frac{4bK_e}{T^2K_3} +$$
$$[y_0(t)-3y_0(t-1)+3y_0(t-2)-y_0(t-3)]\frac{8aK_e}{T^3K_3} =$$
$$[V_m(t)+3V_m(t-1)+3V_m(t-2)+V_m(t-3)]$$

where position output $y_o(t)$, motor voltage $V_m(t)$, sample period T, rotation-to-position gain constant $K_3$ and motor resistance R have known values. The parameters $x_2(t)$ and $K_e$ are unknowns that respectively represent load function and motor torque constants. The parameters a and b are also unknowns representing functions of mechanical moment of inertia, motor inductance, motor resistance and motor torque constants.

The four unknowns in equation (8) can be determined by reducing results from repeated measurements of the known parameters from the servo system. Specifically, the parameter for motor voltage, $V_m(t)$, in equation (8) can be defined as:

$$\Psi(t)=V_m(t)+3V_m(t-1)+3V_m(t-2)+V_m(t-3) \quad (9)$$

Furthermore, the parameter for position output, $y_o(t)$, from equation (8) can be defined as:

$$\Phi 1(t) = y_0(t)-3y_0(t-1)+3y_0(t-2)-y_0(t-3) \quad (10)$$
$$\Phi 2(t) = y_0(t)-y_0(t-1)-y_0(t-2)+y_0(t-3)$$
$$\Phi 3(t) = y_0(t)+y_0(t-1)-y_0(t-2)-y_0(t-3)$$

Matrices can then be defined using the known parameters measured within the servo system using a time spacing of m sample periods of T, for n samples. The matrices can be defined as follows:

$$\Phi = \begin{bmatrix} 1 & \Phi 3(t) & \Phi 2(t) & \Phi 1(t) \\ 1 & \Phi 3(t-m) & \Phi 2(t-m) & \Phi 1(t-m) \\ 1 & \Phi 3(t-2m) & \Phi 2(t-2m) & \Phi 1(t-2m) \\ \vdots & \vdots & \vdots & \vdots \\ 1 & \Phi 3(t-[n-1]m) & \Phi 2(t-[n-1]m) & \Phi 1(t-[n-1]m) \end{bmatrix} \quad (11)$$

$$\Psi = \begin{bmatrix} \Psi(t) \\ \Psi(t-m) \\ \Psi(t-2m) \\ \vdots \\ \Psi(t-[n-1]m) \end{bmatrix} \quad \Omega = \begin{bmatrix} 8RX_2/K_e \\ 2K_e/(TK_3) \\ 4bK_e/(T^2K_3) \\ 8aK_e/(T^3K_3) \end{bmatrix} \cong \begin{bmatrix} \Omega_1 \\ \Omega_2 \\ \Omega_3 \\ \Omega_4 \end{bmatrix}$$

From relationships defined in equations (9), (10) and (11) and repeated measurements for the known parameters from the servo system, the matrix version of equation (8) is:

$$\Psi = \Phi\Omega \quad (12)$$

where the matrix $\Omega$ contains the unknowns from equation (8) that are to be solved. The solution for $\Omega$ using the Gaussian least-squares fit process over a specified range is:

$$\Omega = (\Phi^T\Phi)^{-1}\Phi^T\Psi \quad (13)$$

Finally, the unknowns, $K_e$, $x_2(t)$, b and a can be determined using $\Omega$ and known parameters, T, $K_3$ and R:

$$K_e = \Omega_2 / [2/(TK_3)] \quad (14)$$

$$x_2 = \Omega_1 / [8R/K_e] \quad (15)$$

$$b = \Omega_3 / [4K_e/(T^2 K_3)] \quad (16)$$

$$a = \Omega_4 / [8K_e/(T^3 K_3)] \quad (17)$$

Equations (14), (15), (16) and (17) provide useful information for the motion subsystem, which includes motor-load element 202 of servo system 200. Rather than use presumed native motion control parameters for feedback and feed forward, which are estimated parameters assigned for use in a model, the present disclosure demonstrates how to determine native motion parameters for use in a servo system using real-time data measured from available hardware data in motor-load element 202. Furthermore, the parameters J and L, respectively the mechanical moment of inertia and the motor inductance, can be determined from equations (4), (16) and (17), as expressed in the following relationships:

$$J = bK_e^2/R \quad (18)$$

$$L = aK_e^2/J \quad (19)$$

As disclosed herein, the parameters $K_e$, J and L, which are native parameters associated with motion control for a servo system, are calculated in real time using data obtained from periodic measurements of available servo system data. In the operation of an actual servo system, some of the blocks in FIG. 2 can be implemented in a computer and functions for those blocks accomplished with software programming to solve, for example, the time domain equivalents of Laplace transform equations. Other elements in the servo system can take the form of electronic circuitry, an electric motor, mechanical drive parts and other physical mechanisms.

Figure 4A:
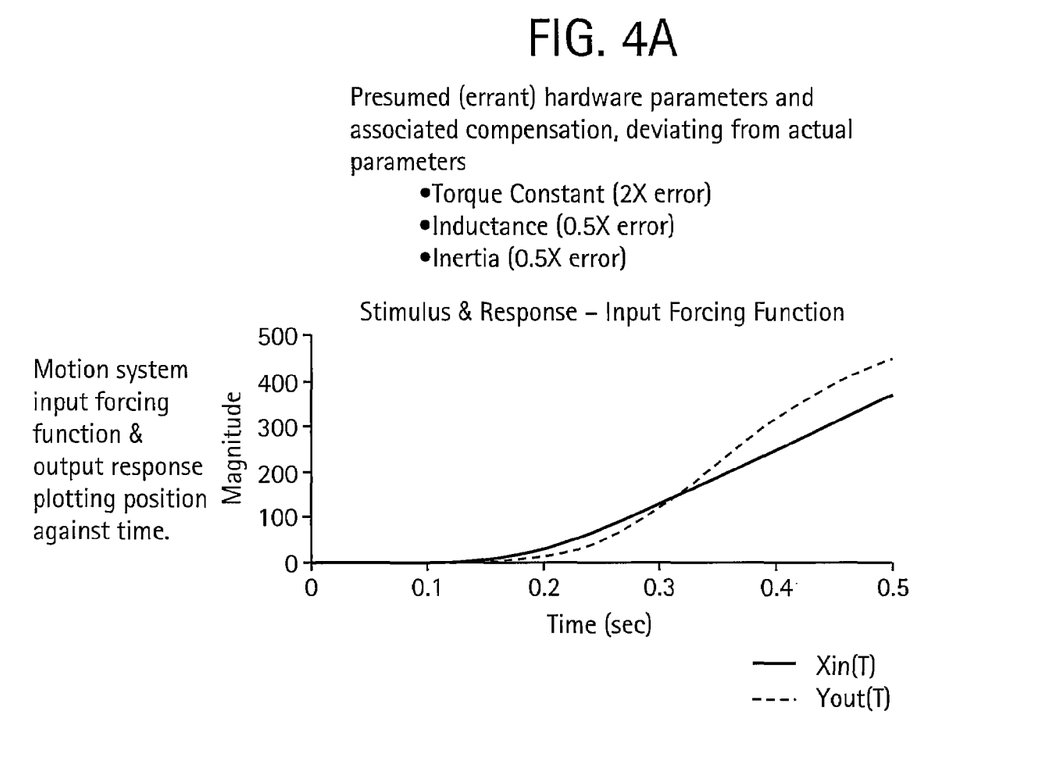
FIG. 4a illustrates a simulated motion system loop response to a collision, using presumed native hardware motion parameters that are in error, according to an embodiment of the present invention.
Figure 4B:
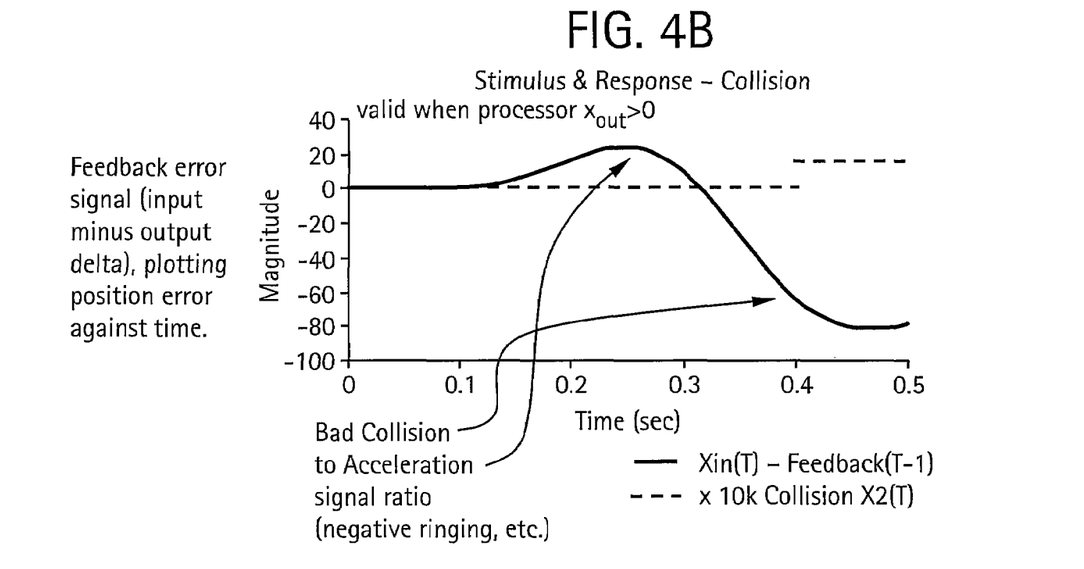
FIG. 4b illustrates a simulated motion system loop response feedback error signal according to an embodiment of the present invention.

FIGS. 4a through 4d show a simulated motion system loop response to a collision function for the topology in FIG. 2 using the motor-load model of FIG. 3 and including feed forward. In FIGS. 4a and 4b, presumed values for native hardware parameters $K_e$ (motor torque constant), L (motor inductance) and J (motion subsystem moment of inertia) containing errors are used for the feedback/feed forward control system. The values for these parameter are set to be in error by a ratio of 2, 0.5 and 0.5, respectively. The feedback/feed forward compensation has been adjusted to match the incorrect parameters, further propagating system performance problems. In FIG. 4a, position forcing function $x_f(t)$ is plotted along with the resulting simulated output response $y_o(t)$. A simulated collision occurs at 0.4 seconds into the plot. The collision function is shown in FIG. 4b along with the feedback error monitor signal, M, previously discussed for the embodiment in FIG. 2. The error signal in FIG. 4b increases in magnitude as the position forcing function $x_f(t)$ accelerates to a constant velocity, and eventually rings negative due to the parameter errors previously described. It is desirable to be able to differentiate between a collision and forcing function acceleration by having a large positive ratio of error signals for these two drivers. However, it is not possible in this situation since the error signal is ill-behaved and rings negative due to the incorrect parameters.

Figure 4C:
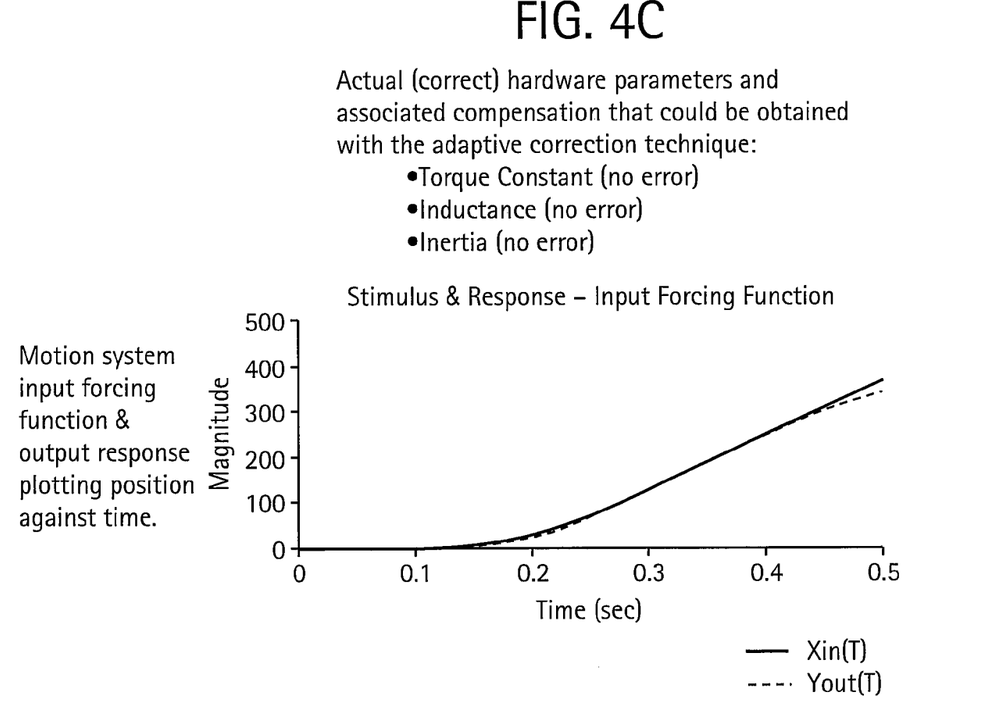
FIG. 4c illustrates a simulated motion system loop response to a collision, using actual native hardware motion parameters that could be reasonably approximately by adaptive correction techniques, according to an embodiment of the present invention.
Figure 4D:
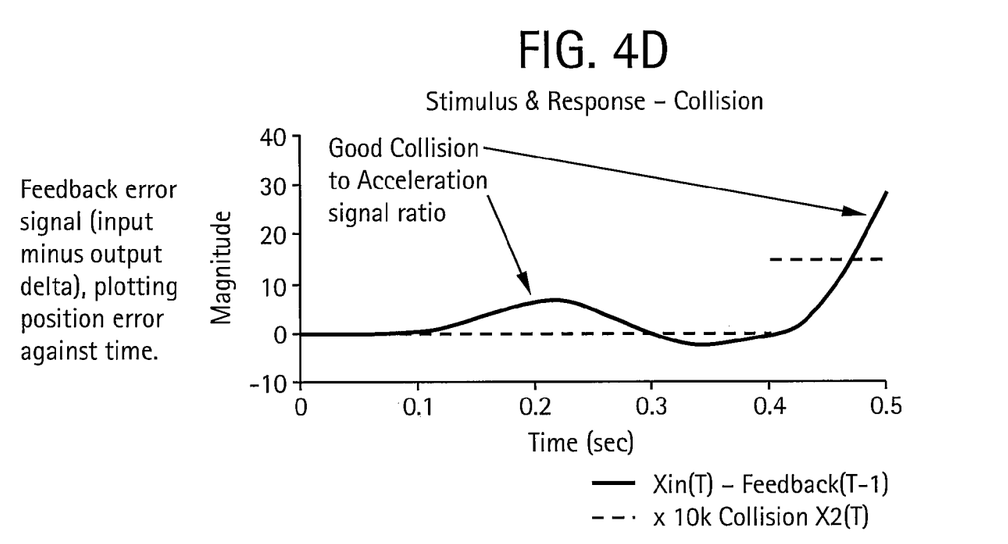
FIG. 4d illustrates a simulated motion system loop response feedback error signal according to an embodiment of the present invention.

In FIGS. 4c and 4d, actual values for native hardware parameters $K_e$ (motor torque constant), L (motor inductance), and J (motion subsystem moment of inertia) are used for the feedback/feed forward control system, with properly matching feedback/feed forward compensation. The actual parameter values can be obtained in real time, for example, applying the embodiments set forth in the present disclosure and culminating in the relationships shown as equations (14) through (19). To facilitate the desired results, the actual or real time native parameters are first used to enhance feedback and feed forward compensation and gain algorithms. The enhanced compensation and gain algorithms can then be used to provide desired coefficients for adjusting the feedback and feed forward algorithms in the computer that can be used to achieve enhanced control signal output from the computer element. The control signal output is used to drive the motor-load element of the servo system. By applying the values for the native motion parameters obtained from real-time data, FIG. 4c demonstrates that the output response $y_o(t)$ more closely tracks the input forcing function $x_f(t)$. FIG. 4d shows that the error ratio between collision and acceleration is now useable for collision detection.

Figure 5:
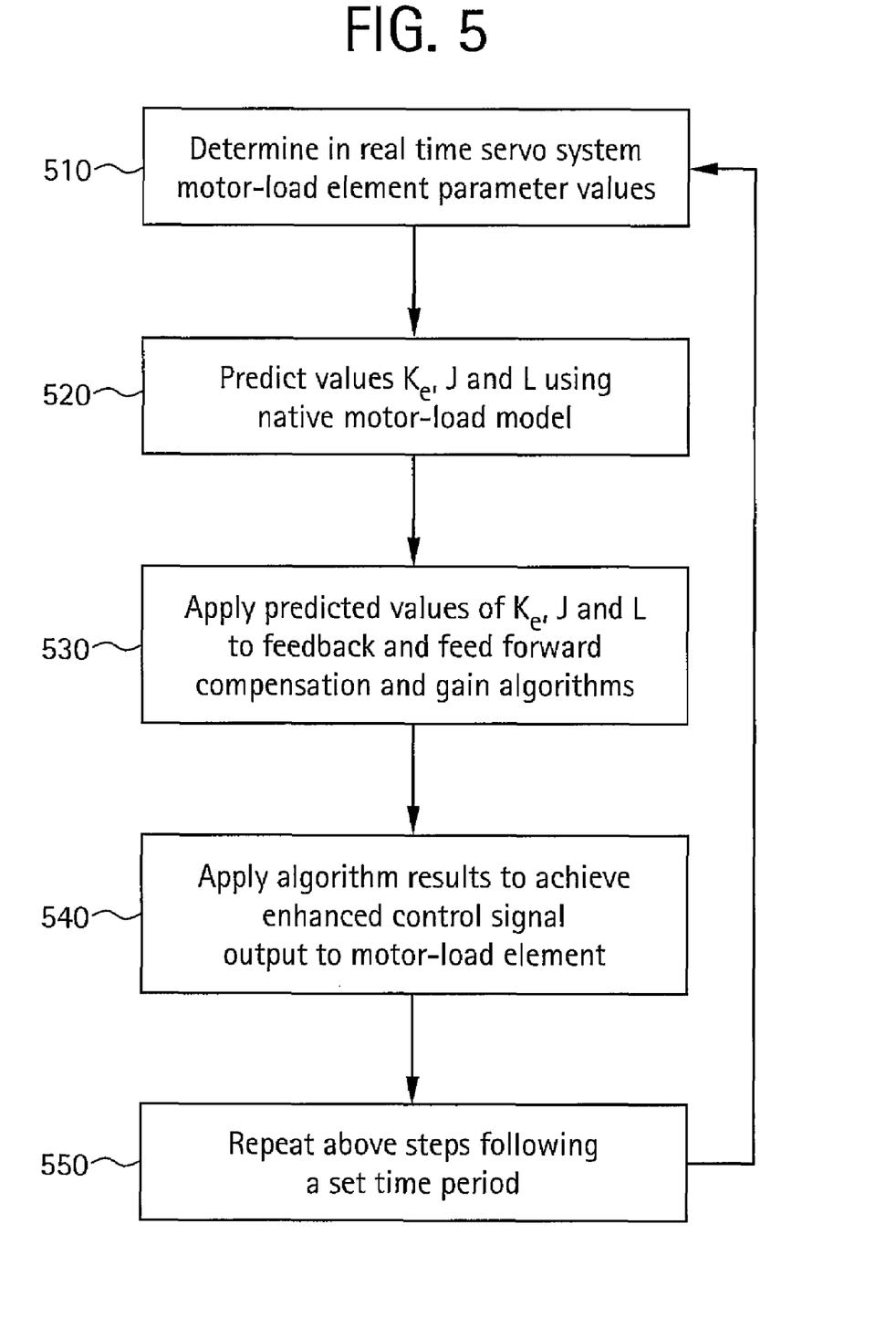
FIG. 5 illustrates a flow diagram for a method for improving collision detection according to an embodiment of the present invention.

FIG. 5 illustrates a method for improving collision detection in an imaging system according to certain embodiments described herein. The first step in the process includes determining in real time the values of certain parameters in a servo system 510 such as position output $y_o(t)$, motor voltage $V_m(t)$, sample period T, rotation-to-position gain constant $K_3$ and motor resistance R. Some parameters, such as $y_o$, may be measured. Other parameters, such as $V_m$, may already be known or have an assigned value. Certain parameters, such as T and $K_3$, may be constants that are known ahead of time. Using these known real-time servo system parameters, a prediction of the motor torque constant $K_e$, mechanical moment of inertia J and/or the motor inductance L for the servo system can be made using a native motor-load model 520. The prediction can be made using a servo system computer. The real-time based predicted values of $K_e$, J and/or L can then be applied to enhance feedback and/or feed forward compensation and gain algorithms 530. The behavioral results of the compensation and gain algorithms can then be applied to adjust the feedback and/or feed forward algorithms in the computer to achieve enhanced control signal output from the computer element driving the motor-load element of the servo system 540. The process can then be repeated 550 following the lapse of a sample period T.

Certain embodiments can include a computer-readable medium having a set of instructions as described in the present disclosure for execution on a computer. The technical effect of such instructions are to improve collision detection in an imaging device using a real-time process for adaptively obtaining motion parameters of a movable component of an imaging system. The set of instruction can include a monitoring routine for determining a servo system motor-load element parameter value in real-time. A prediction routine can also be included for applying the real-time servo system motor-load parameter value into a native motor-load model. The native motor-load model is used to predict a motion control parameter value. This can be followed by the implementation of a control signal routine that applies the predicted motion control parameter value to an operation that modifies a control signal output of a computer element of a servo system. Other embodiments can include a subroutine for measuring a position output $y_o$ of an imaging receptor, a radiation source, and/or an object, such as a patient. The instructions for the prediction routine can also predicting a motion control parameter value for motor torque constant $K_e$, mechanical moment of inertia J, and/or motor inductance L for the motor-load element of the servo system. Further embodiments can include a routing routine for extracting known servo system motor-load element parameter values.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims. Furthermore, as used herein, an element or step recited in the singular and preceded with the word "a" or "an" should be understood as not excluding plural elements or steps, unless such exclusion is explicitly recited.

The invention claimed is:

1. An imaging system comprising:
   a radiation source;
   an image receptor located to receive radiation emitted by said radiation source; and
   a servo system comprising a computer operationally coupled to a motor-load element, said servo system configured to position at least one of said radiation source, said image receptor, and an object to be scanned, wherein said servo system is configured to measure at set time intervals in real-time a position of at least one of said radiation source, said image receptor, and said object, wherein said measured position is used to calculate a native hardware motion parameter value for said servo system.

2. The imaging system of claim 1, wherein said servo system is further configured to utilize at set time intervals at least one of a motor voltage and a motor-to-position gain constant of said motor-load element, wherein said motor voltage and said motor rotation-to-gain constant is used to calculate a native hardware motion parameter value for said servo system.

3. The imaging system of claim 1, wherein said calculated native hardware motion parameter value is used to determine a control signal to be sent from said computer to said motor-load element.

4. The imaging system of claim 3, wherein said control signal is determined using servo system feedback and feed forward compensation and gain algorithms that include said native hardware motion parameter value.

5. The imaging system of claim 1, wherein said calculated native hardware motion parameter includes at least one of a motor torque constant, mechanical moment of inertia and motor inductance for said motor-load element of said servo system.

6. The imaging system of claim 1, wherein said calculation of said native hardware motion parameter value is obtained using a native motor-load model of said motor-load element for said servo system.

7. The imaging system of claim 1, wherein said calculated native hardware motion parameter value is applied to at least one of a feedback compensation algorithm and a feed forward compensation algorithm operating in said computer.

8. The imaging system of claim 1, wherein a feedback mechanism is used to determine said position of at least one of said radiation source, said image receptor and said object.

9. The imaging system of claim 1, further comprising a C-arm and a support structure, said support structure capable of holding said C-arm in a suspended position, said support structure further mounted to a wheeled base, wherein said image receptor and said radiation source are mounted at opposing locations on the C-arm.

10. A method of improving collision detection between an object and an electromechanical system having a mechanical output controlled by a servo system, said method comprising:

(a) determining servo system motor-load element parameter values in real-time;
   (b) calculating in a native motor-load model a motion control parameter value for a motor-load element of said servo system using at least one of said real-time servo system motor-load element parameter values; and
   (c) applying said calculated motion control parameter value in an operation within a computer element of said servo system to enhance a control signal output from said computer element to said motor-load element of said servo system.

11. The improved collision detection method of claim 10, wherein said determination of servo system motor-load element parameter values in real-time includes measuring a position output $y_o$ of at least one of an imaging receptor, radiation source, and an object.

12. The improved collision detection method of claim 11, wherein said imaging receptor and said radiation source are mounted at opposing locations on a C-arm of an imaging device.

13. The improved collision detection method of claim 10, wherein said determination of servo system parameter values further comprises extracting a motor-load element parameter value for motor voltage $V_m(t)$.

14. The improved collision detection method of claim 10, wherein said calculation of a motion control parameter value includes calculating at least one of motor torque constant $K_e$, mechanical moment of inertia J, and motor inductance L for the motor-load element of said servo system.

15. The improved collision detection method of claim 10, wherein said operation within said computer element comprises applying said calculated motion control parameter value to at least one of a feedback compensation algorithm and a feed forward compensation algorithm.

16. The improved collision detection method of claim 10, wherein a feedback mechanism is used to measure a motor-load element parameter value.

17. A computer-readable medium having a set of instructions for execution on a computer, said set of instructions comprising:
   a monitoring routine for determining a servo system motor-load element parameter value in real-time;
   a calculation routine for applying said real-time servo system motor-load parameter value into a native motor-load model to calculate a motion control parameter value; and
   a control signal routine that applies said calculated motion control parameter value to an operation that modifies a control signal output of a computer element of a servo system.

18. The computer readable medium of claim 17, wherein said set of instructions for said monitoring routine further includes a subroutine for measuring a position output $y_o$ of at least one of an imaging receptor, a radiation source, and an object.

19. The computer readable medium of claim 17, wherein said set of instructions for said calculation routine includes calculating a motion control parameter value for at least one of motor torque constant $K_e$, mechanical moment of inertia J, and motor inductance L for said motor-load element of said servo system.

20. The computer readable medium of claim 17, further comprising a routine for extracting known servo system motor-load element parameter values.

* * * * *